US011497861B2

(12) United States Patent
Hartung et al.

(10) Patent No.: US 11,497,861 B2
(45) Date of Patent: Nov. 15, 2022

(54) MEDICAL INJECTION DEVICE (71) Applicant: B. BRAUN MELSUNGEN AG, Melsungen (DE)

(72) Inventors: Jürgen Hartung, Helsa (DE); Christin Kiehle, Melsungen (DE); Volker Klute, Melsungen (DE); Jan Koot, Homberg (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 54 days.

(21) Appl. No.: 16/137,056

(22) Filed: Sep. 20, 2018

(65) Prior Publication Data
US 2019/0091419 A1 Mar. 28, 2019

(30) Foreign Application Priority Data

Sep. 27, 2017 (DE) .......................... 102017217236.3

(51) Int. Cl.
*A61M 5/50* (2006.01)
*A61M 5/31* (2006.01)
(Continued)

(52) U.S. Cl.
CPC .............. *A61M 5/504* (2013.01); *A61M 5/31* (2013.01); *A61M 5/3134* (2013.01);
(Continued)

(58) Field of Classification Search
CPC .. A61M 2005/5053; A61M 2005/5046; A61M 5/504; A61M 5/5013; A61M 5/00;
(Continued)

(56) References Cited

U.S. PATENT DOCUMENTS 5,176,639 A  1/1993 Pozzi et al.
5,613,951 A  3/1997 Meyer et al.
(Continued)

FOREIGN PATENT DOCUMENTS

CN  1038766 A  1/1990
EP  2153856 A1  2/2010
(Continued)

OTHER PUBLICATIONS

Extended European Search Report for European Application No. 18 191 673.5, dated Oct. 5, 2018, with partial translation, 10 pages.
German Search Report for German Application No. 10 2017 217 236.3, dated May 23, 2018, with partial translation—10 pages.
Office Action received in Chinese Application No. 201811132187.5 dated Oct. 18, 2021, with translation, 21 pages.

*Primary Examiner* — Kevin C Sirmons
*Assistant Examiner* — Alexandra Lalonde
(74) *Attorney, Agent, or Firm* — Christopher A. Rothe; Culhane Meadows, PLLC (57) ABSTRACT

An injection device includes a cylinder having a cavity for receiving a liquid. A passage is connected to the cavity for inflow and/or outflow of the liquid. The passage can be connected to an injection component. A shut-off valve has a valve body and a flexible sealing ring with an opening. The valve body, proceeding from a release position in which the passage is freed, is at least partially movable through the opening of the sealing ring to a blocking position in which the valve body engages behind the opening so that movement of the valve body to the release position is blocked and the passage is sealed off against proximally directed flow. An adapter body is connected to the cylinder. The shut-off valve is arranged at a proximal end of the adapter body and at a distal end of the cylinder. The device can be used in a syringe.

17 Claims, 5 Drawing Sheets

(51) Int. Cl.
*A61M 5/315* (2006.01)
*A61M 5/34* (2006.01)

(52) U.S. Cl.
CPC ...... *A61M 5/3158* (2013.01); *A61M 5/31513* (2013.01); *A61M 5/34* (2013.01); *A61M 2005/3128* (2013.01); *A61M 2005/5053* (2013.01)

(58) Field of Classification Search
CPC ........ A61M 5/348; A61M 5/50; A61M 5/508; A61M 5/31513; A61M 5/34; A61M 5/345; A61M 5/347; A61M 5/344; A61M 5/343; A61M 2005/506; A61M 2005/3128; A61M 2039/1077; A61M 5/32; A61M 5/16804; A61M 5/16813; A61M 5/16881; A61M 5/346; A61M 5/3134; A61M 39/22; A61M 39/24; A61M 2039/226; A61M 2039/2433; A61M 2039/2473; A61M 2039/2486; A61M 2205/0216
See application file for complete search history.

(56) References Cited

U.S. PATENT DOCUMENTS

| | | | |
|---|---|---|---|
| 6,663,591 B1 | 12/2003 | d'Ussel | |
| 2006/0084915 A1* | 4/2006 | Chang | A61M 5/322 604/110 |
| 2010/0030146 A1* | 2/2010 | Kakish | A61M 5/504 604/110 |
| 2016/0158523 A1* | 6/2016 | Helm | A61M 39/10 604/513 |
| 2018/0289941 A1* | 10/2018 | Di Ubaldi | A61M 5/3134 |

FOREIGN PATENT DOCUMENTS

| | | | | |
|---|---|---|---|---|
| WO | 9204064 A1 | 3/1992 | | |
| WO | WO-9204064 A1 * | 3/1992 | ......... | A61M 5/5013 |
| WO | 9323099 A1 | 11/1993 | | |

\* cited by examiner

MEDICAL INJECTION DEVICE

RELATED APPLICATION(S)

This application claims the benefit of priority of German patent application DE 10 2017 217 236.3, the contents of which is incorporated by reference herein in its entirety.

FIELD

The present disclosure relates to a medical injection device for single use in the administration of a liquid, with a hollow cylinder, which has a cavity for receiving the liquid and has a distal end, with a passage which is arranged in the region of the distal end of the hollow cylinder and is fluidically connected to the cavity and is provided for the inflow and/or outflow of the liquid from the cavity, with a connection portion for releasable fluid-tight connection to a complementary mating connection portion of an injection component arranged in such a way that the passage can be fluidically connected to a lumen of the injection component, and with a shut-off valve arrangement which has a valve body and a flexible sealing ring with an opening and which is arranged and/or configured in such a way that, by means of a flow of the liquid directed distally through the passage, the valve body, proceeding from a release position in which the passage is freed, is at least partially movable in the distal direction through the opening of the sealing ring to a blocking position in which the valve body engages behind the opening in such a way that a movement of the valve body to the release position is blocked and the passage is sealed off against a proximally directed flow.

BACKGROUND

An injection device of this kind is known from EP 2 153 856 B1. The known injection device has a hollow cylinder with a cavity for receiving a liquid that is to be administered. The cavity is fluidically connected to a distally arranged passage. Moreover, the injection device has a connection portion in the shape of a male Luer connector part formed on the hollow cylinder. This male Luer connector part is releasably connected in a fluid-tight manner to a female Luer connector part of an injection component referred to as an assembly. At its distal end, the injection component has an injection needle. The passage is fluidically connected to a lumen of the injection component designated as a recess. By the effect of a piston moved in the distal direction in the hollow cylinder, liquid from the cavity can be forced through the passage and through the lumen out of the injection needle and thus administered to a patient. In order to prohibit a repeat use of the injection device and thereby prevent transmission of pathogens, a shut-off valve arrangement is provided. The latter has a flexible sealing ring, with an opening, and a valve body. During the administration of the liquid, and by means of the distally directed flow of the liquid here, the valve body, proceeding from a release position in which the passage is freed, is moved in the distal direction through the opening of the sealing ring to a blocking position. In this blocking position, time valve body engages behind the opening in such a way that a movement of the valve body to the release position is blocked and the passage is sealed off against a proximally directed flow. In this way, the known injection device is safeguarded against the cavity being filled again with liquid. In the known injection device, the shut-off valve arrangement is arranged in the recess of the injection component, which necessitates a corresponding configuration of the injection component.

SUMMARY

The object of the present disclosure is to make available an injection device of the type mentioned at the outset, which has a simplified structure and which in particular permits use in conjunction with a standardized injection component, in particular a disposable cannula.

This object is achieved by the fact that an adapter body is provided having a proximal end, which is connected with force-fit and/or form-fit engagement to the distal end of the hollow cylinder, and a distal end, on which the connection portion is formed, wherein the shut-off valve arrangement is arranged at the proximal end of the adapter body and at the distal end of the hollow cylinder. By virtue of the solution according to the present disclosure, it is possible in particular to omit arranging the shut-off valve arrangement on the injection component and it is thus possible to manage without a special configuration of the injection component. This is because, according to the present disclosure, an adapter body is provided which at one end, namely at its distal end, is provided for releasable connection to a preferably standardized injection component and at the other end, namely at its proximal end, is connected to the hollow cylinder. The adapter body thus forms a kind of bridging piece between the hollow cylinder and the injection component. According to the present disclosure, the shut-off valve arrangement is arranged here at the proximal end of the adapter body and at the distal end of the hollow cylinder, such that the injection device is usable in conjunction with a conventional injection component, i.e. conventional in the sense of not being equipped with a shut-off valve arrangement. Moreover, the hollow cylinder and the adapter body are configured, according to the present disclosure, as separately manufactured structural elements, such that in particular the connection portion of the adapter body can be configured independently of the hollow cylinder, and vice versa. Manufacturing advantages can be achieved in this way. At its proximal end, the adapter body is connected to the hollow cylinder preferably by means of a form-fit latching connection and/or a frictional clamping connection. The connection of this kind can be releasable or preferably non-releasable. The adapter body is manufactured, for example, as an injection-molded plastic part. The connection portion can be configured, for example, in the form of a preferably male Luer slip or Luer lock connector of a kind already known in principle. Alternatively, it is possible that the connection portion has another kind of configuration, preferably a standardized one. The connection portion is provided for connecting the adapter body and thus the injection device to a mating connection portion of complementary shape of an injection component which is, for example, in the form of a cannula, a hose or similar configuration. The shut-off valve arrangement is advantageously actuated by the actual medium, such that the injection device can be blocked off against further use by means of a substantially complete emptying of the liquid through the passage, and no further handling is needed. The shut-off valve arrangement is preferably secured partially on the hollow cylinder and partially on the adapter body. For example, the sealing ring can be secured at the proximal end of the adapter body and the valve body can be secured at the distal end of the hollow cylinder, or vice versa. The terms proximal and distal denote a position that is closer to or further away from, respectively, a respective reference point.

In one embodiment, the hollow cylinder has an integrally molded cylinder base, wherein the valve body is guided axially movably on a guide path extending through the cylinder base. The guide path can extend in the form of a preferably circular cylindrical bore, recess or the like through the cylinder base. For the purpose of guiding on the guide path, the valve body preferably has a shaft portion. If the guide path is configured as a circular cylindrical bore, the shaft portion can have a bolt-shaped configuration and can be fitted in a slidingly movable manner into the through bore. The cylinder base limits the cavity in the distal direction. The passage preferably extends through the cylinder base.

In a further embodiment, the sealing ring has a clamping portion which is fixed by form-fit engagement, in particular clamped, in the axial direction and/or in the radial direction between the hollow cylinder, in particular the cylinder base, and the adapter body. The clamping portion is preferably arranged at a proximal front end of the sealing ring and can be configured, for example, in the form of a radial flange, a collar or the like. The clamping portion is preferably fixed by form-fit engagement between the distal end of the hollow cylinder and the proximal end of the adapter body. This embodiment permits particularly simple assembly of the injection device.

In a further embodiment, the lumen of the adapter body has a proximally arranged receiving portion in which the sealing ring is fitted. The lumen is in the form of a continuous opening which extends through the adapter body in the axial direction. In relation to a further course of the lumen, the receiving portion of the lumen can be widened or narrowed in the radial direction. Particularly simple fitting of the sealing ring is achieved if the receiving portion is arranged at a proximal front end region of the lumen.

In a further embodiment, the receiving portion has an undercut radial groove open at one side in the proximal direction, wherein the sealing ring engages behind the radial groove and is thus fixed with form-fit engagement on the adapter body in the proximal direction. On account of the resulting form-fit connection of the sealing ring to the receiving portion, the latter, during manufacture of the injection device, can be secured captively on the adapter body before the adapter body is connected to the hollow cylinder. This permits simple handling during a final assembly of the injection device, to be more precise during connection of the hollow cylinder to the adapter body.

In a further embodiment, the distal end of the hollow cylinder has a latch portion which latches with a complementary mating latch portion of the adapter body, preferably non-releasably, in such a way that the adapter body is fixed in the axial direction on the hollow cylinder. The latch portion can have one or more latching lugs, latching hooks or latching teeth, and the mating latch portion can accordingly have latch openings, latch grooves or the like of complementary shape, or vice versa. By means of the latch connection of this kind, the hollow cylinder and the adapter body are fixedly connected to each other at least in the axial direction, such that inadvertent withdrawal of the adapter body from the hollow cylinder, or vice versa, is counteracted.

In a further embodiment, the distal end of the hollow cylinder has a profile portion, preferably in the form of a multi-tooth arrangement, which meshes with a complementary mating profile portion of the adapter body in such a way that the adapter body is fixed in the circumferential direction on the hollow cylinder. Accordingly, an anti-rotation means is obtained between the hollow cylinder and the adapter body. Improved handling of the injection device can be permitted in this way.

In a further embodiment, the latch portion and/or the profile portion is formed on a circumferential collar portion of the hollow cylinder, which collar portion extends distally with respect to the cavity, in particular with respect to the cylinder base. The collar portion is preferably configured in one piece with the hollow cylinder. The collar portion preferably has a round, preferably circular cross section. The collar portion can be produced as a continuous single wall portion or alternatively can be formed by separate individual wall portions. The injection device can be made easy to handle and produce if the collar portion is oriented parallel, preferably coaxial, to a jacket wall of the hollow cylinder.

In a further embodiment, the valve body has, at its distal end, a radially widened head portion. The head portion can in particular have a spherical or mushroom-head-shaped basic shape. The dimensions of the head portion are advantageously adapted to the diameter of the opening of the sealing ring in such a way that, proceeding from the release position, and by means of a flow of the liquid directed distally through the passage, the head portion is movable through the opening of the sealing ring and engages behind this opening with form-fit engagement in the blocking position.

In a further embodiment, the head portion has a radially tapered continuation extending in the distal direction. The front end of the continuation can be provided with a run-on bevel. By means of the continuation, an improved centring of the valve body in the opening of the sealing ring can be achieved in particular.

BRIEF DESCRIPTION OF THE DRAWING FIGURES

Further advantages and features will become clear from the following description of exemplary embodiments depicted in the following drawings.

DETAILED DESCRIPTION

Figure 1:
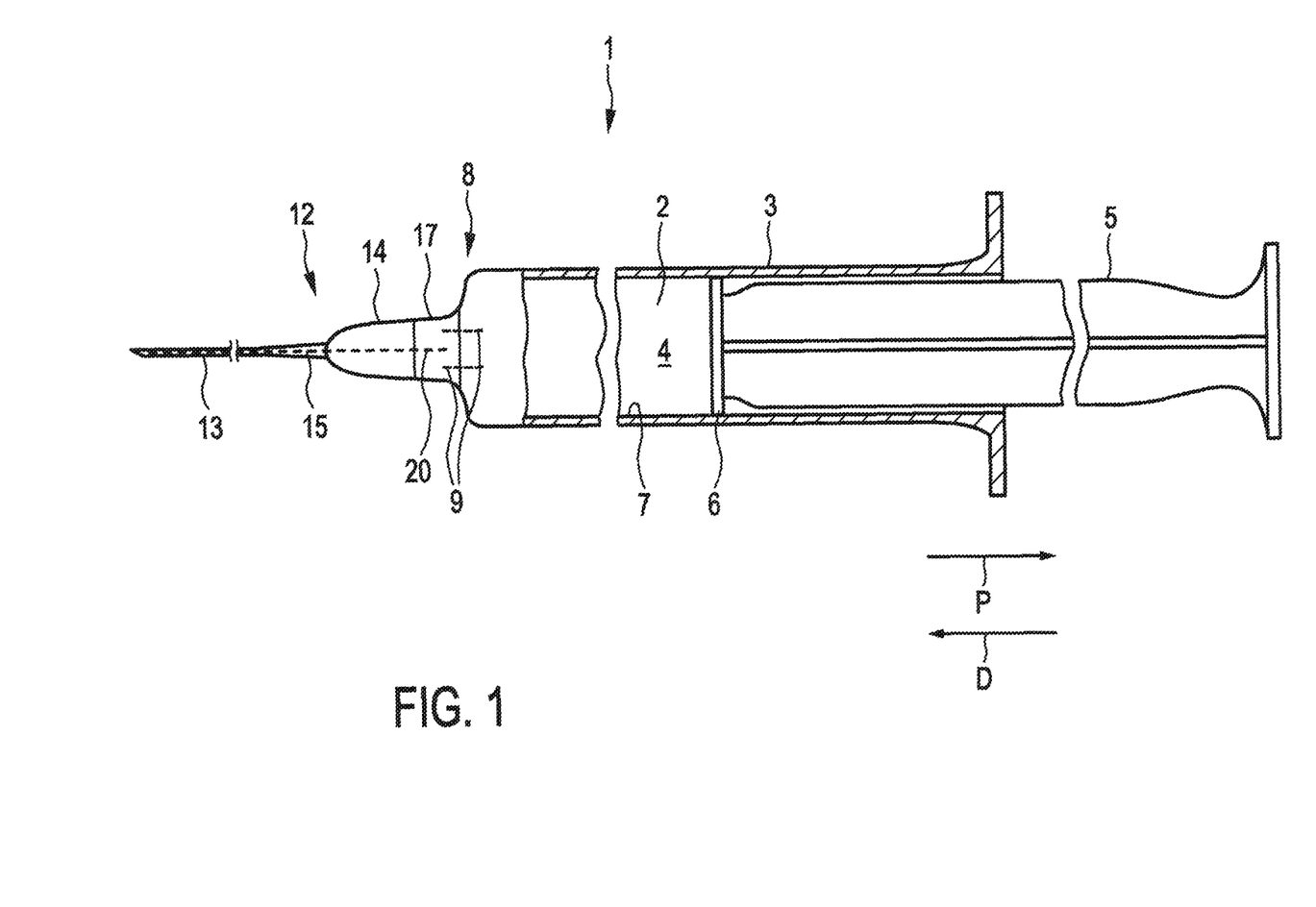
FIG. 1 shows a schematic, partially sectional side view of an embodiment of an injection device according to the present disclosure, which is connected releasably to an injection component in the form of a disposable cannula.

A medical injection device 1 according to FIG. 1 is configured in the form of a disposable syringe and is provided for single use in the administration of a medical liquid 2.

Figure 2:
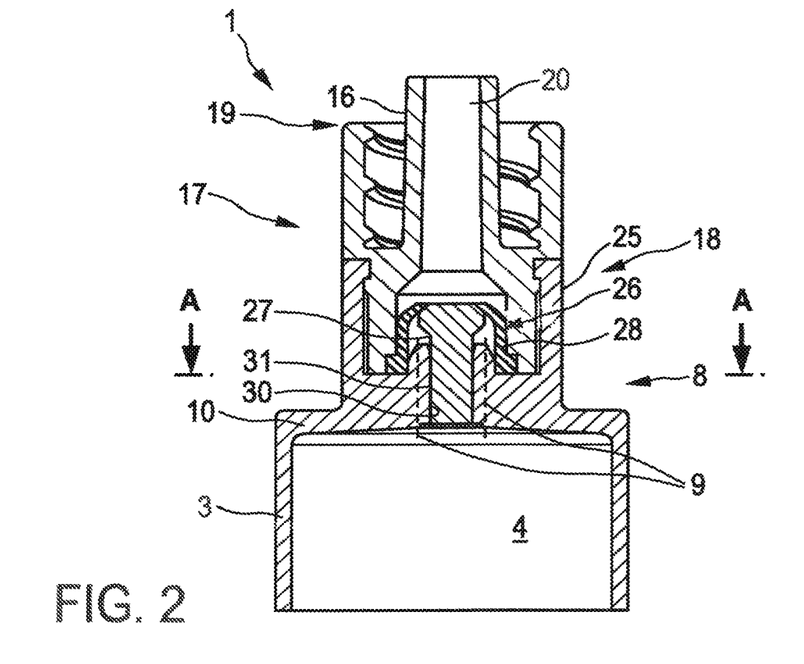
FIG. 2 shows a schematic longitudinal section through the injection device according to FIG. 1 in the region of a shut-off valve arrangement.
Figure 5:
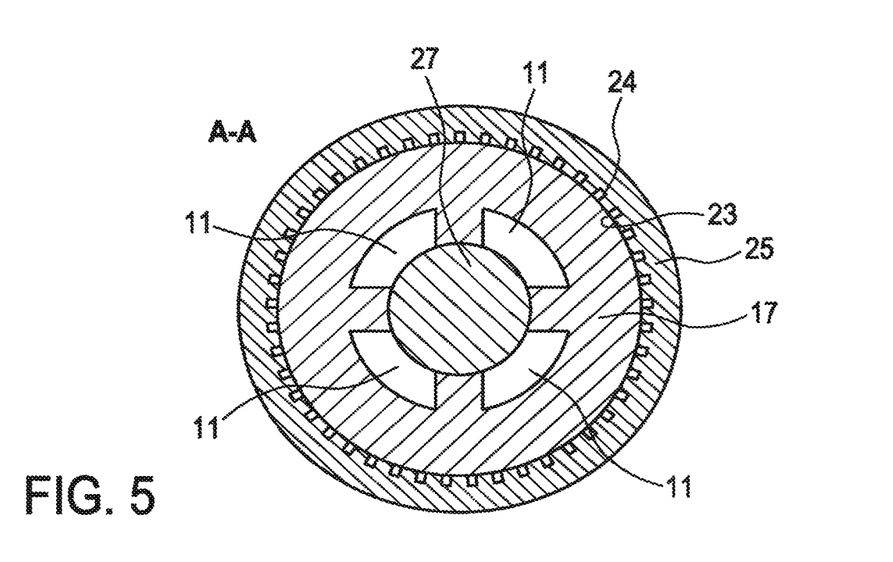
FIG. 5 shows the injection device according to FIGS. 1, 2 and 4 in a schematic cross-sectional view along a section line A-A according to FIG. 2.

The injection device 1 has a hollow cylinder 3 with a cavity 4 for receiving the liquid 2. For manual actuation of the injection device, an actuating ram 5 with a piston 6 arranged at the front end is provided. The piston 6 seals off the cavity 4 in a fluid-tight manner in the proximal direction P and is movable by sliding in the axial direction with respect to an inner wall 7 of the hollow cylinder 3. At the distal end 8 of the hollow cylinder 3, a passage 9 is arranged which, in FIG. 1, is indicated only by means of two broken lines. The passage 9 is fluidically connected to the cavity 4 and is provided for the inflow and outflow of the liquid 2 from the cavity 4. As can be seen in particular from FIG. 2, the passage 9 extends through a cylinder base 10 which is integrally molded on the hollow cylinder 3 and which delimits the cavity 4 in the distal direction D. It will be seen from the cross-sectional view in FIG. 5 that the passage 9 is formed by four openings 11. The openings 11 are offset by 90° from each other in the circumferential direction and are arranged concentrically to a central longitudinal axis of the hollow cylinder 3 and each have the shape of a segment of a circle. At its distal end, the injection device 1 is connected to an injection component in the form of a disposable cannula 12. The disposable cannula 12 has a hypodermic injection needle 13 and a needle attachment 14. The disposable cannula 12 is of a design known in principle and has in particular a continuous lumen 15, indicated by a broken line in FIG. 1. The lumen 15 of the disposable cannula 12 is connected fluidically to the passage 9 and to the cavity 4 in a manner that will be described in detail below. For connection to the disposable cannula 12, the injection device 1 has a connection portion 16 (FIG. 2). The connection portion 16 is configured in the form of a male Luer lock portion and, in a manner known in principle but not explained in any more detail, is connected in a fluid-tight manner and releasably to a mating connection portion of the disposable cannula 12, which mating connection portion is configured in the form of a female Luer lock portion and is arranged on the needle attachment 14.

Figure 4:
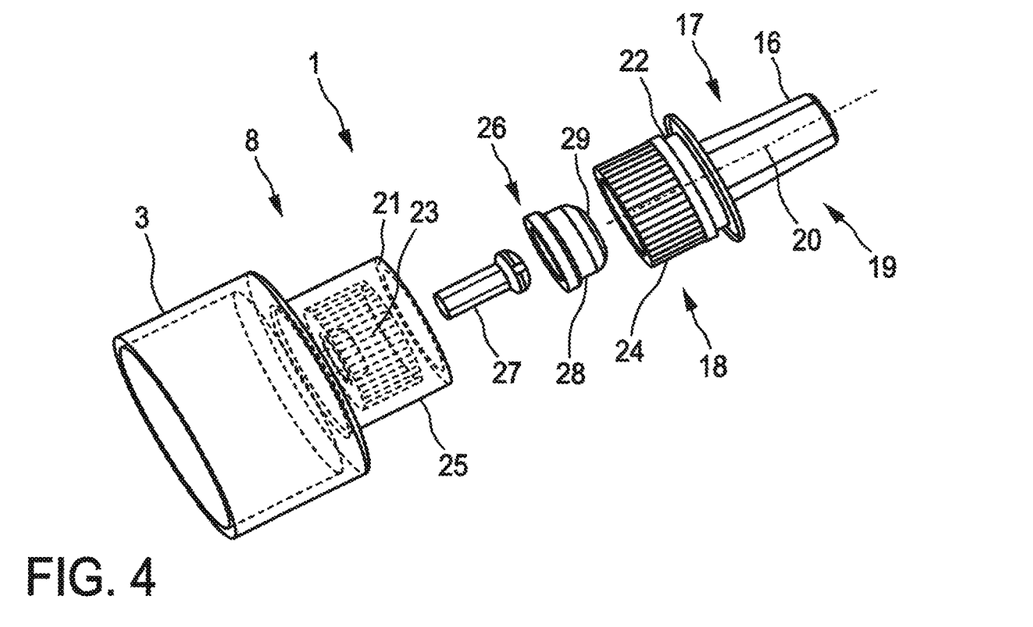
FIG. 4 shows a schematic, perspective exploded view of the injection device according to FIGS. 1 and 2 in the region of the shut-off valve arrangement.

As will be seen in particular from FIGS. 2 and 4, an adapter body 17 is provided having a proximal end 18, which is connected to the distal end 8 of the hollow cylinder 3 by force-fit and/or form-fit engagement, and having a distal end 19, on which the connection portion 16 is formed. Moreover, the adapter body 17 has a lumen 20 in the form of a continuously extending opening. One end of the lumen 20 is fluidically connected to the lumen 15 of the disposable cannula 12 and the other end is fluidically connected, in a manner to be described in detail below, to the passage 9 and thus to the cavity 4. The adapter body 17 is configured as a structural part produced separately from the hollow cylinder 3, preferably as an injection-molded plastic part, and is connected to the hollow cylinder 3 by means of a form-fit latching connection and a multiple-tooth connection. For this purpose, the distal end 8 of the hollow cylinder 3 has a latch portion 21. The latch portion 21 is locked to a complementary mating latch portion 22 of the adapter body 17, such that the adapter body 17 is fixed in the axial direction on the hollow cylinder 3 (FIG. 4). The latch portion 21 is configured in the form of a latching lug that extends in the circumferential direction. Complementing the latter, the adapter body 17 has a latching groove extending in the circumferential direction and serving as mating latch portion 22. The multiple-tooth connection is formed between a profile portion 23, formed at the distal end 8 of the hollow cylinder 3, and a complementary mating profile portion 24 of the adapter body 17. In this way, the adapter body 17 is fixed in the circumferential direction on the hollow cylinder 3 and is secured against undesired rotation. The profile portion 23 is in the form of a multi-tooth arrangement which extends continuously in the circumferential direction and which has a multiplicity of longitudinal grooves extending in the axial direction. Accordingly, the mating profile portion 24 is configured in the form of an outer toothing adapted in terms of dimensions to the inner toothing of the profile portion 23.

Both the latch portion 21 and the profile portion 23 are formed on a circumferential collar portion 25 of the hollow cylinder 3, which collar portion 25 extends distally with respect to the cavity 4, more precisely with respect to the cylinder base 10. The collar portion 25 extends in the form of a cylinder bushing which is open at its distal end in the axial direction and is delimited at its proximal end by the cylinder base 10. The collar portion 25 has a circular cylindrical cross section and is oriented substantially coaxially to a central longitudinal axis of the hollow cylinder 3. Moreover, the collar portion 25 has a smaller diameter than the hollow cylinder 3 and is formed in one piece with the cylinder base 10 and to this extent in one piece with the hollow cylinder 3.

Moreover, the injection device 1 has a shut-off valve arrangement 26 with a valve body 27 and a flexible sealing ring 28 with an opening 29. The shut-off valve arrangement 26 is arranged at the proximal end 18 of the adapter body 17 and at the distal end 8 of the hollow cylinder 3.

The valve body 27 is guided axially movably on a guide path 30 extending through the cylinder base 10. The guide path 30 extends in the form of a circular cylindrical bore axially through the cylinder base 10. The internal diameter of the guide path 30 is adapted to an external diameter of a shaft portion 31 of the valve body 27 in such a way that the latter is fitted smoothly and in a substantially fluid-tight manner into the guide path 30.

The sealing ring 28, at any rate in its undeformed configuration shown in particular in FIG. 2, has a cap-shaped or bell-shaped basic form. Both in the axial direction and in the radial direction, the sealing ring 28 is fixed with form-fit engagement between the hollow cylinder 3, more precisely the cylinder base 10, and the adapter body 17. For this purpose, the sealing ring 28 has a clamping portion 32. The clamping portion 32 can be seen in particular in detail from FIGS. 6 to 8 and is formed at a proximal end of the sealing ring 28 in the form of a radial flange. In order to arrange the sealing ring 28 on the adapter body 17, the proximal end 18 thereof is shaped accordingly. Thus, the lumen 20 of the adapter body 17 has a receiving portion 33. Compared to a further extent of the lumen 20, the receiving portion 33 is in the radial direction to receive the sealing ring 28 and additionally has a radial groove 34 open at one end in the proximal direction. The clamping portion 32 of the sealing ring 28 is widened and fitted into the radial groove 34 of the receiving portion 33.

Figure 6:
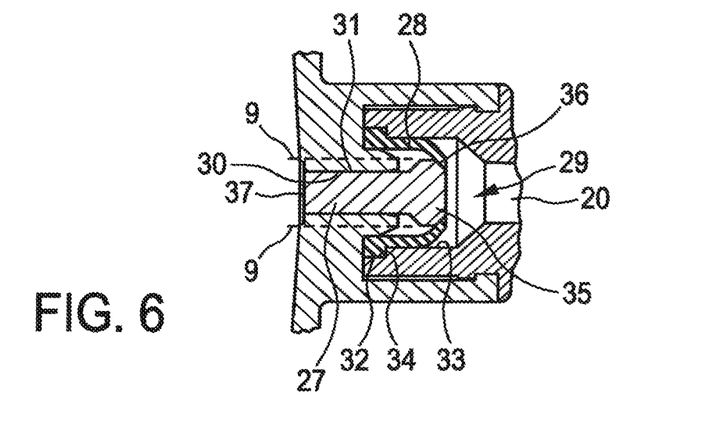
FIGS. 6 to 8 each show a partial longitudinal section through the shut-off valve arrangement of the injection devices according to FIGS. 1 to 5 in different positions during a movement from a release position to a blocking position.
Figure 7:
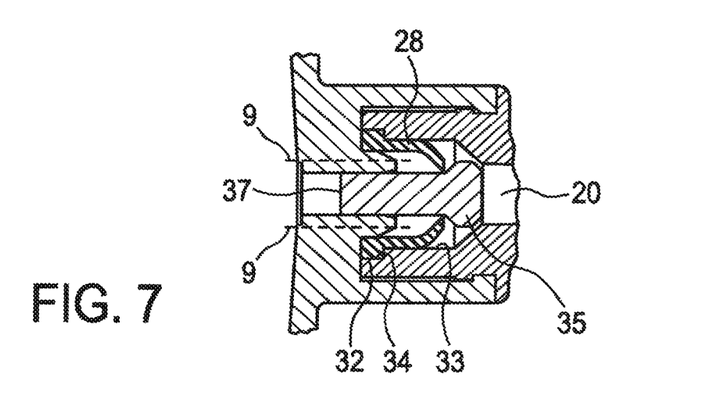
Figure 8:
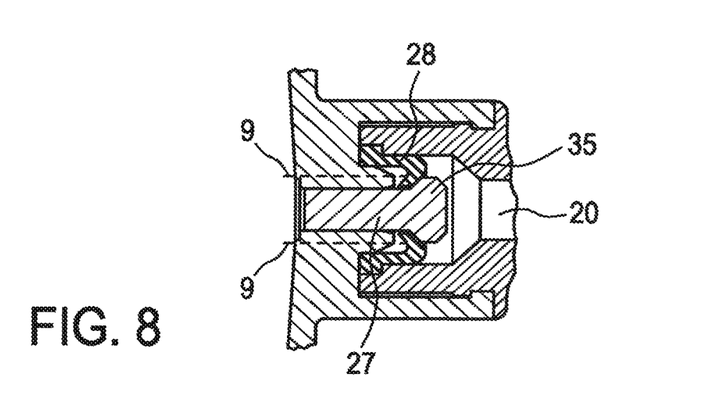

As will be seen in particular from FIGS. 6 to 8, the valve body 27 has, at its distal end, a head portion 35 that is radially widened compared to the shaft portion 31. The head portion 35 has the shape of the head of a mushroom and, in terms of its external diameter, is adapted to the internal diameter of the opening 29 of the sealing ring 28. The function of the shut-off valve arrangement 26 and the interaction of the valve body 27 with the sealing ring 28 will be discussed in greater detail below, particularly with reference to FIGS. 6 to 8.

Proceeding from the configuration of the shut-off valve arrangement 26 shown in FIG. 6, and designated as the release position, the injection device 1 can be filled with liquid in a fundamentally known manner by means of a movement of the actuating ram 5 in the proximal direction P. Here, the piston 6 is moved in the proximal direction P with respect to the inner wall 7 of the hollow cylinder 3 and, from a liquid reservoir (not shown in detail) fluidically connected to the lumen 20 of the adapter body 17, sucks liquid through the lumen 20, the opening 29, and a radial gap 36 formed between the head portion 35 of the valve body 27 and the sealing ring 28, into the openings 11 of the passage 9 and onwards into the cavity 4 of the hollow cylinder 3. In the process, the valve body 27 remains on a side of the opening 29 directed towards the passage 9, which does not substantially differ from the position seen in FIG. 6.

In order to empty the injection device 1, the piston 6 is moved in the distal direction D via the actuating ram 5 and pressure is thus applied to the cavity 4. On account of this application of pressure, the liquid 2 flows out of the cavity 4, through the openings 11 of the passage 9 and the radial gap 36 into the lumen 20 of the adapter body 17. Provided that the disposable cannula 12 is connected to the adapter body 17, as is shown by way of example in FIG. 1, the liquid 2 passes further from the lumen 20 into the lumen 15 as far as an outlet opening of the injection needle 13 and can thus be administered to a patient. Here, the shut-off valve arrangement 26 is configured in such a way that, by means of a flow of the liquid 2 thus directed distally, the valve body 27, proceeding from the release position shown in FIG. 6, is moved through the opening 29 of the sealing ring 28. This axial movement of the valve body 27 in the distal direction D is effected by pressure applied to a proximal front end 37 and axially projected surface of the head portion 35 directed towards the passage 9. As a result of the flexible configuration of the sealing ring 28, the opening 29 initially widens under such a movement of the valve body 27 and, after complete passage of the head portion 35, bears on the shaft portion 31 of the valve body 27. In such a blocking position as illustrated in FIG. 7, the valve body 27 accordingly engages behind the opening 29. Accordingly, renewed filling of the injection device 1 with liquid is prevented. The reason is that, proceeding from the configuration shown in FIG. 7, the valve body 27 is aspirated towards the left, with respect to the drawing plane of FIGS. 6 to 8, on account of a proximally directed displacement of the piston 6 caused by negative pressure. Here, on the one hand, the passage 9 is sealed off on account of a sealing contact between the sealing ring 28 and the head portion 35. On the other hand a further movement of the valve body 27 in the proximal direction P is suppressed by means of the sealing ring 28. Here, the sealing ring 28 is flexibly deformed and curves inwards and produces a form-fit connection to the head portion 35. Re-use of the injection device 1 is prevented in this way.

Figure 3:
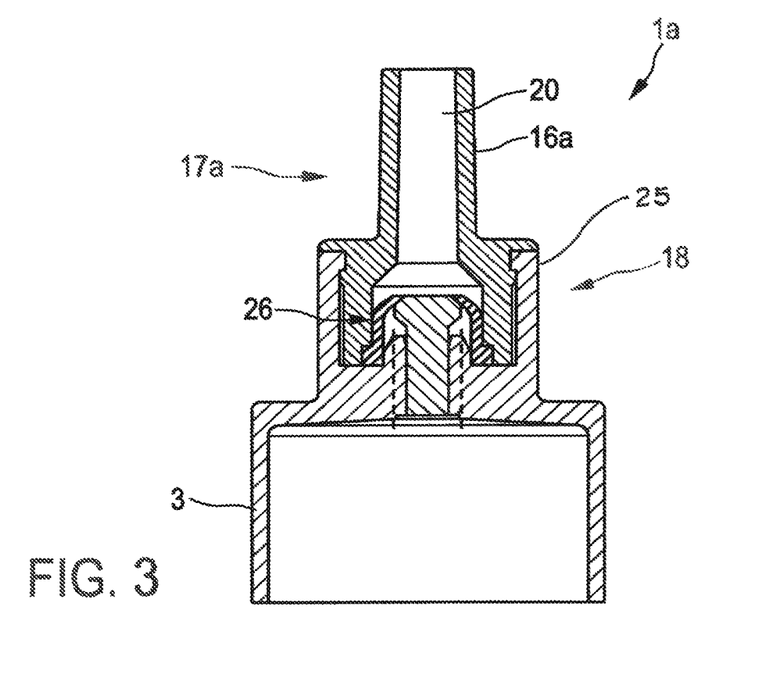
FIG. 3 shows a further embodiment of an injection device according to the present disclosure in a longitudinal section according to FIG. 2.
Figure 9:
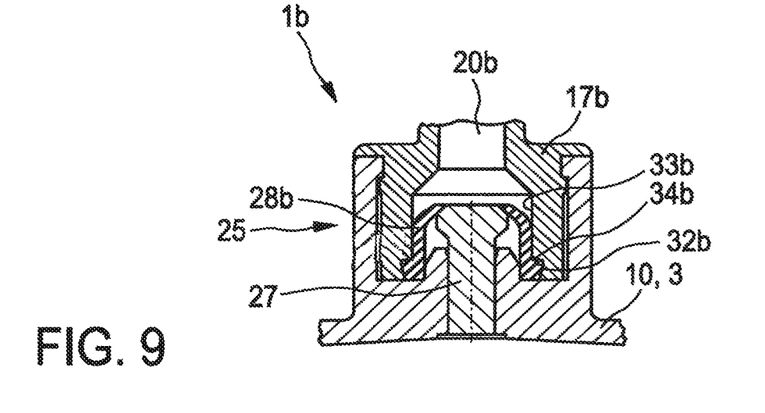
FIG. 9 shows a further embodiment of an injection device according to the present disclosure in a partial schematic longitudinal section.
Figure 10:
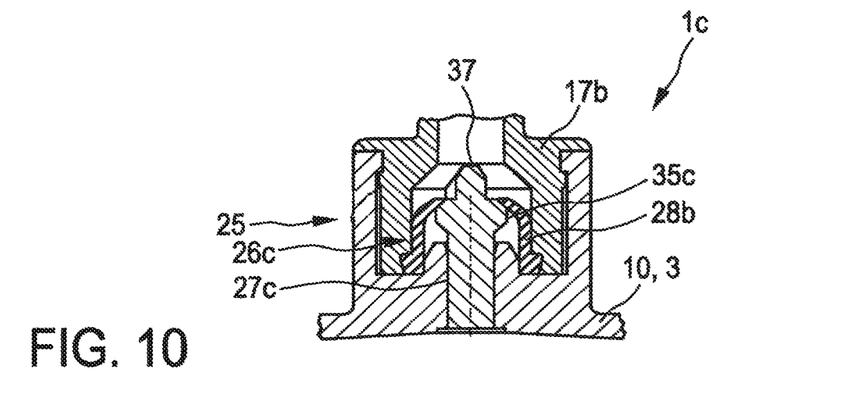
FIG. 10 shows a further embodiment of an injection device according to the present disclosure in a view corresponding to FIG. 9.

Further embodiments of injection devices 1a, 1b, 1c according to the present disclosure can be seen in FIGS. 3, 9 and 10. The embodiments according to FIGS. 3, 9 and 10 correspond substantially to the embodiment described above with reference to FIGS. 1, 2 and 4 to 8. Therefore, in order to avoid repetition, reference is made to the disclosure concerning the embodiment according to the last-mentioned figures. Only the essential differences of the respective embodiment according to FIGS. 3, 9 and 10 are discussed below. Parts and sections of the injection devices 1a to 1c that are identical to the injection device 1 are provided in this respect with identical reference signs. Parts and sections which are of identical function, but which differ in terms of their structure, are designated by the same reference signs with the addition of lowercase letters.

The injection device 1a according to FIG. 3 differs from the injection device 1 (FIG. 2) in that an adapter body 17a is provided which, instead of a Luer lock portion, has a connection portion 16a configured in the form of a Luer slip portion. In particular, the hollow cylinder 3 and the collar portion 25 provided for connection to the adapter body 17a are unchanged. Accordingly, the hollow cylinder 3 can be produced independently of the configuration of the connection portion 16, 16a, and vice versa. Advantages in terms of manufacture and assembly can be achieved in this way.

By contrast, the injection device 1b according to FIG. 9 differs substantially in terms of a different configuration of the form-fit engagement between a sealing ring 28b and an adapter body 17b. To be more exact, a receiving portion 33b of a lumen 20b is provided with an undercut radial groove 34b. A radial groove 34b is open at one side in the proximal direction P, and the groove base tapers radially in the proximal direction P. A clamping portion 32b of the sealing ring 28b is shaped to complement the groove profile of the radial groove 34b and thus engages behind the latter with form-fit engagement in the proximal direction. Before the adapter body 17b and the collar portion 25 of the hollow cylinder 3 are joined together at the time of manufacture, the sealing ring 28b can thus be secured captively on the adapter body 17b. This in particular permits simplified handling during assembly.

The injection device 1c according to FIG. 10 differs from the injection device 1b according to FIG. 9 only in that the valve body 27c in that case has a modified head portion 35c. The head portion 35c has a radially tapered continuation 37 extending in the distal direction.

The invention claimed is:

1. A medical injection device for single use in administration of a liquid, the medical injection device comprising:
 a hollow cylinder having a proximal end, a distal end opposite the proximal end, and a longitudinal axis extending from the proximal end to the distal end through an axial center of the hollow cylinder, the hollow cylinder further comprising a cavity for receiving the liquid and a passage arranged in a region of the distal end of the hollow cylinder, the passage being fluidically connected to the cavity for inflow and/or outflow of the liquid from the cavity, the hollow cylinder further comprising a cylinder base and a circumferential collar portion at the distal end of the hollow cylinder;
 an adaptor body received inside the circumferential collar portion at the distal end of the hollow cylinder, the adaptor body comprising a connection portion for releasable fluid-tight connection to a complementary mating connection portion of a liquid receiving component arranged in such a way that the passage can be fluidically connected to a lumen of the liquid receiving component; and
 a shut-off valve arrangement which has a valve body and a flexible sealing ring with an opening and which is arranged and/or configured in such a way that, by virtue of a flow of the liquid directed distally through the passage, the valve body, proceeding from a release position is at least partially movable in a distal direction through the opening of the sealing ring to a blocking position in which the valve body engages the opening in such a way that a movement of the valve body to the release position is blocked and the passage is sealed off against a proximally directed flow, the adapter body comprising a proximal end, which is connected with force-fit and/or form-fit engagement to the distal end of the hollow cylinder, and a distal end, on which the connection portion is formed, and having a lumen fluidically connected to the passage, wherein the shut-off valve arrangement is arranged at the proximal end of the adapter body and at the distal end of the hollow cylinder, and the valve body being positioned in and movable through the cylinder base, wherein the distal end of the hollow cylinder has a first plurality of linear teeth extending parallel to the longitudinal axis of the hollow cylinder, wherein the proximal end of the adapter body comprises a second plurality of linear teeth extending parallel to the longitudinal axis of the hollow cylinder, and wherein the first plurality of linear teeth meshes with the second plurality of linear teeth in such a way that the adapter body is fixed in a circumferential direction on the hollow cylinder.

2. The medical injection device according to claim 1, wherein movement of the valve body is guided axially on a guide path extending through the cylinder base.

3. The medical injection device according to claim 1, wherein the sealing ring has a clamping portion which is fixed by form-fit engagement in an axial direction and/or in a radial direction between the hollow cylinder and the adapter body.

4. The medical injection device according to claim 1, wherein the lumen of the adapter body has a proximally arranged receiving portion in which the sealing ring is fitted.

5. The medical injection device according to claim 1, wherein the distal end of the hollow cylinder has a latch portion which latches with a complementary mating latch portion of the adapter body in such a way that the adapter body is fixed in an axial direction on the hollow cylinder.

6. The medical injection device according to claim 5, wherein the latch portion is formed on the circumferential collar portion of the hollow cylinder, wherein the circumferential collar portion extends distally with respect to the cavity.

7. The medical injection device according to claim 1, wherein the first plurality of linear teeth forms a first plurality of longitudinal grooves extending in an axial direction, and the second plurality of linear teeth forms a second plurality of longitudinal grooves extending in the axial direction.

8. The medical injection device according to claim 7, wherein the first plurality of linear teeth is formed on the circumferential collar portion of the hollow cylinder, wherein the circumferential collar portion extends distally with respect to the cavity.

9. The medical injection device according to claim 1, wherein the valve body has, at the distal end of the valve body, a radially widened head portion.

10. The medical injection device according to claim 1, wherein the valve body has, at the distal end of the valve body, a head portion with a radially tapered continuation extending in the distal direction.

11. The medical injection device according to claim 1, wherein the connection portion is a Luer connection portion.

12. The medical injection device according to claim 11, wherein the Luer connection portion comprises a Luer lock portion.

13. The medical injection device according to claim 11, wherein the Luer connection portion comprises a Luer slip portion.

14. The medical injection device according to claim 1, wherein the complementary mating connection portion of the liquid receiving component is a hub of a disposable needle cannula.

15. The medical injection device according to claim 1, wherein the first plurality of linear teeth is arranged continuously in the circumferential direction in the circumferential collar portion, and the second plurality of linear teeth is arranged continuously in the circumferential direction on the adaptor body.

16. A medical injection device for single use in administration of a liquid, the medical injection device comprising:

a hollow cylinder comprising a proximal end, a distal end opposite the proximal end, and a longitudinal axis extending from the proximal end to the distal end through an axial center of the hollow cylinder, the hollow cylinder further comprising a cavity for receiving the liquid, and a passage arranged in a region of the distal end, the passage being fluidically connected to the cavity for inflow and/or outflow of the liquid from the cavity, the hollow cylinder further comprising a cylinder base and a circumferential collar portion at the distal end of the hollow cylinder;

an adaptor body received inside the circumferential collar portion at the distal end of the hollow cylinder, the adaptor body comprising a connection portion for releasable fluid-tight connection to a complementary mating connection portion of a liquid receiving component arranged in such a way that the passage can be fluidically connected to a lumen of the liquid receiving component; and a shut-off valve arrangement which has a valve body and a flexible sealing ring with an opening, the shut-off valve arrangement configured in such a way that, by virtue of a flow of the liquid directed distally through the passage, the valve body, proceeding from a release position is at least partially movable in a distal direction through the opening of the sealing ring to a blocking position in which the valve body engages the opening in such a way that a movement of the valve body to the release position is blocked and the passage is sealed off against a proximally directed flow, the adapter body comprising a proximal end connected to the distal end of the hollow cylinder, and a distal end, on which the connection portion is formed, and having a lumen fluidically connected to the passage, wherein the shut-off valve arrangement is arranged at the proximal end of the adapter body and at the distal end of the hollow cylinder, the valve body being positioned in and movable through the cylinder base, the sealing ring comprising a circumferential flange at a proximal end of the sealing ring, and the lumen of the adapter body having a proximally arranged receiving portion in which the sealing ring is fitted, wherein the receiving portion has an undercut radial groove inside the adapter body that is open at the proximal end of the adapter body, wherein the undercut radial groove receives the circumferential flange of the sealing ring in a form-fit engagement to fix the sealing ring to the adapter body, wherein the distal end of the hollow cylinder has a first plurality of linear teeth extending parallel to the longitudinal axis of the hollow cylinder, wherein the proximal end of the adapter body comprises a second plurality of linear teeth extending parallel to the longitudinal axis of the hollow cylinder, and wherein the first plurality of linear teeth meshes with the second plurality of linear teeth in such a way that the adapter body is fixed in a circumferential direction on the hollow cylinder.

17. A medical injection device for single use in administration of a liquid, the medical injection device comprising:

a hollow cylinder comprising a proximal end, a distal end opposite the proximal end, and a longitudinal axis extending from the proximal end to the distal end through an axial center of the hollow cylinder, the hollow cylinder further comprising a cavity for receiving the liquid and a passage arranged in a region of the distal end of the hollow cylinder, the passage being fluidically connected to the cavity for inflow and/or outflow of the liquid from the cavity, the hollow cylinder further comprising an integrally molded cylinder base and a circumferential collar portion at the distal end of the hollow cylinder;

an adaptor body received inside the circumferential collar portion at the distal end of the hollow cylinder, the adaptor body comprising a connection portion for releasable fluid-tight connection to a complementary mating connection portion of a liquid receiving component arranged in such a way that the passage can be fluidically connected to a lumen of the liquid receiving component; and a shut-off valve arrangement which has a valve body and a flexible sealing ring with an opening and which is arranged and/or configured in such a way that, by virtue of a flow of the liquid directed distally through the passage, the valve body, proceeding from a release position is at least partially movable in a distal direction through the opening of the sealing ring to a blocking position in which the valve body engages the opening in such a way that a movement of the valve body to the release position is blocked and the passage is sealed off against a proximally directed flow, the adapter body comprising a proximal end, which is connected with force-fit and/or form-fit engagement to the distal end of the hollow cylinder, and a distal end, on which the connection portion is formed, and having a lumen fluidically connected to the passage, wherein the shut-off valve arrangement is arranged at the proximal end of the adapter body and at the distal end of the hollow cylinder, and the valve body being positioned in and movable through the cylinder base, wherein the distal end of the hollow cylinder has a first plurality of linear teeth extending parallel to the longitudinal axis of the hollow cylinder, wherein the proximal end of the adapter body comprises a second plurality of linear teeth extending parallel to the longitudinal axis of the hollow cylinder, and wherein the first plurality of linear teeth meshes with the second plurality of linear teeth in such a way that the adapter body is fixed in a circumferential direction on the hollow cylinder.

\* \* \* \* \*